United States Patent [19]

Miller et al.

[11] Patent Number: 5,070,204

[45] Date of Patent: Dec. 3, 1991

[54] PROCESS FOR PREPARATION OF FLUOROMETHYL-SUBSTITUTED PYRIDINE DICARBOXYLATES

[75] Inventors: William Miller, Glendale; Mitchell J. Pulwer, St. Louis, both of Mo.

[73] Assignee: Monsanto Company, St. Louis, Mo.

[21] Appl. No.: 495,185

[22] Filed: Mar. 19, 1990

[51] Int. Cl.$^5$ ............... C07D 211/90; C07D 213/80; C07D 213/803

[52] U.S. Cl. ................................. 546/321; 546/250; 546/322

[58] Field of Search .................. 546/322, 321, 250

[56] References Cited

U.S. PATENT DOCUMENTS 4,618,679 10/1986 Lee ........................................ 546/220
4,692,184 9/1987 Lee ............................................ 71/94

FOREIGN PATENT DOCUMENTS 0135491 3/1985 European Pat. Off. ................ 71/94

OTHER PUBLICATIONS

Chemical Abstracts, vol. 88, (17), abst. No. 121,534c Apr. 24, 1978.
Chemical Abstracts, vol. 99, (23), abst. No. 194,576e Dec. 5, 1983.
Fieser and Fieser, Reagents for Organic Synthesis, vol. 2, pp. 99–101, Wiley-Interscience Publishers QD 262 F.5 (1969).
Raphael et al., Advances In Organic Chemistry, vol. 5, Interscience Publishers, QD 251 A3 C.2 (1965).

*Primary Examiner*—Alan L. Rotman
*Attorney, Agent, or Firm*—Stanely M. Tarter; James C. Bolding; Howard C. Stanley

[57] ABSTRACT

Described herein is a process for preparation of substituted pyridine dicarboxylate compounds.

12 Claims, No Drawings

PROCESS FOR PREPARATION OF FLUOROMETHYL-SUBSTITUTED PYRIDINE DICARBOXYLATES

Methods for preparation of 2,6-bis(fluorinated methyl)-pyridine dicarboxylates and pyridine dicarbothioates are disclosed in U.S. Pat. Nos. 4,692,184 and 4,618,679 and in European Patent 135,491. These compounds are useful as herbicides.

DESCRIPTION OF THE PRIOR ART

As used herein, the following terms have the following meanings:
DABCO—1,4-diazabicyclo-[2.2.2]-octane
DBU—1,8-diazabicyclo-[5.4.0]-undec-7-ene
ETFAA—ethyl 4,4,4-trifluoro-3-oxo-butanoate
IVA—isovaleraldehyde, or 3-methyl-butanal
NMR—nuclear magnetic resonance
GLC—gas-liquid chromatography
% Assay—weight % desired product compound
% Yield—100 x mols desired product/mol initial IVA starting material.

NOTE: Where a yield is shown herein in discussing the effect of varying a process parameter, all process variables not explicitly shown to be varied are held constant.

As outlined in Scheme I, preparation of diethyl 2-difluoromethyl-4-(2-methylpropyl)-6-trifluoromethyl-3,5-pyridinedicarboxylate is accomplished by a Hantzsch-type base catalyzed intermolecular cyclization of ethyl 4,4,4-trifluoro-3-oxo-butanoate (ethyl trifluoroacetoacetate, or ETFAA) and isovaleraldehyde to form a substituted dihydroxypyran, followed by ammonolysis. Dehydration of the resultant dihydroxypiperidines gives a mixture of 1,4 and 3,4 dihydropyridine isomers.

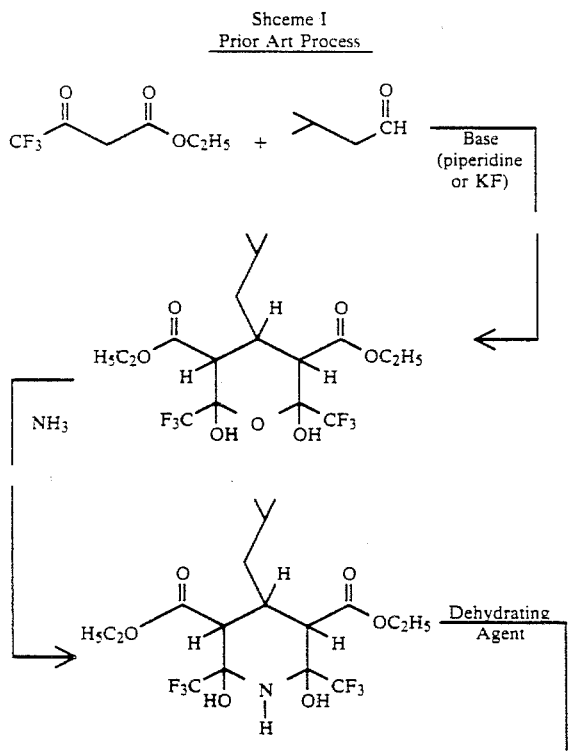

Shceme I
Prior Art Process

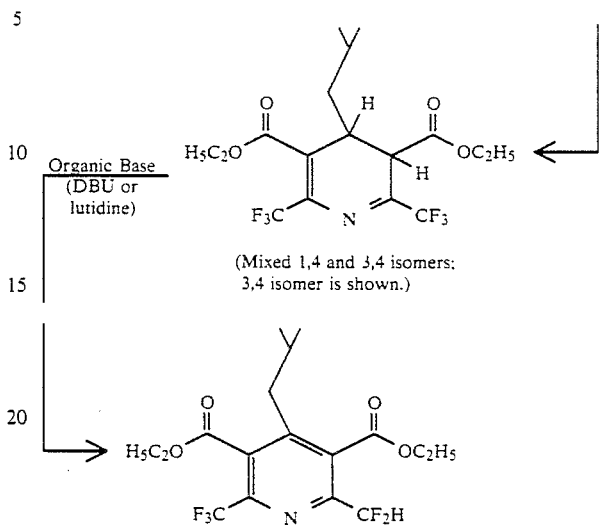

(Mixed 1,4 and 3,4 isomers; 3,4 isomer is shown.)

Dehydrofluorination of the dihydropyridines using an organic base such as DBU or 2,6-lutidine affords good yields (80% overall) of the pyridine diethylester. Examples 14 and 16 of U.S Pat. No. 4,692,184 are reproduced below in relevant part and are illustrative of the prior art.

EXAMPLE 14 OF U.S. Pat. No. 4,692,184

Preparation of dimethyl 2-(difluoromethyl)-6-(trifluoromethyl)-4-isobutyl-3,5-pyridinedicarboxylate (a) Dehydrofluorination Using DBU A mixture of 23.0 g (0.0591 mole) of the dihydropyridine, 12.2 g (0.077 mole) of 96% pure DBU, and 100 ml of THF is held at reflux for 3 days and poured into 250 ml of 3N HCl. The oil precipitate is extracted into ether (2×100 ml). The ether extracts are dried (MgSO4) and concentrated to give 14.4 g of an oil which, contained the desired product and acidic products. This oil is dissolved in ether and extracted with 100 ml of saturated sodium bicarbonate. The ether layer is dried (MgSO4) and concentrated to give 8.9 g of an oil which is 71% pure desired product.

The sodium bicarbonate extract is acidified with concentrated HCl to give an oil which is extracted into ether. The ether layer is dried (MgSO4) and concentrated to give 4.8 g of a residue which contained monocarboxylic acid and dicarboxylic acid (9:1) derived from the desired product. This residue is treated with 3.0 g (0.0217 mole) of potassium carbonate, 20 ml of methyl iodide, and 50 ml of acetone. The mixture is held at reflux for 42 hours and concentrated. The residue is treated with water and extracted with ether (2×100 ml). The ether layer is dried and concentrated. The residue is kugelrohr distilled at 1 torr (pot temperature of 130° C.) to give 5.1 g (23.4% from the dihydropyridine) of the desired product. The 71% pure desired product described previously was chromatographed by HPLC using 3% ethyl acetate/cyclohexane as eluent to give an earlier fraction (0.79 g, retention time 7–8.5 min) which was identified as methyl 6-(difluoromethyl)-4-(isobutyl)-2-(trifluoromethyl)-3-pyridinecarboxylate.

The second fraction is an additional 6.4 g (29.4%) of pure pyridine product.

(b) Dehydrofluorination Using Tributylamine

A mixture of 38.9 g of a 80% pure dihydropyridine and 20.5 g of tributylamine is heated to 155° C. in 30 minutes. The reaction mixture was cooled to 30° C. and diluted with 100 ml of toluene. The toluene solution is washed successively with 6N hydrochloric acid, saturated sodium bicarbonate, and brine, dried and concentrated to give 36.4 g of a 73% pure product which corresponds to a 85% yield. This reaction can also be carried out in excess of tributylamine (10 equivalent) giving essentially similar results.

(c) Dehydrofluorination Using Tributylamine in Toluene

A mixture of 38.9 g of 80% pure dihydropyridine, 20.4 of tributylamine and 30 ml of toluene is heated to 115° C. in 40 minutes and held at 115° C. for 1 hour and 40 minutes. The reaction mixture is cooled and worked up as in (b) to give 36.3 g of a 76% pure product which corresponds to a 90% yield.

(d) Dehydrofluorination Using Triethylamine

A mixture of 11.8 g of 80% pure dihydropyridine and 3.34 g of triethylamine is heated at 100° C. for 10 minutes, then at 125° C. for 10 minutes. The reaction mixture was cooled and worked up as in (b) to give 8.14 g of a 76% pure product which corresponds to a 63% yield.

(e) Dehydrofluorination Using 2,6-Lutidine in the Presence of a Catalytic Amount Of DBU A mixture of 5.0 g of dihydropyridine and 2.13 g of 2,6-lutidine is heated at 143° C. for 30 minutes. Two drops of DBU is added and the reaction mixture is heated for an additional one hour and 30 minutes, cooled and worked up as in (b) to give 4.23 g of the desired product. The reaction can also be carried out in excess of 2,6-lutidine and catalytic amount of DBU without solvent or in the presence of toluene as solvent giving similar results.

EXAMPLE 16 of U.S. Pat. No. 4,692,184

Preparation of diethyl 2-(difluoromethyl)-4-isobutyl-6-(trifluoromethyl)-3,5-pyridinedicarboxylate A mixture of 10.0 g (0.0240 mole) of diethyl 2,6-bis(-trifluoromethyl)-1,4-dihydro-4-isobutyl-3,5-pyridinedicarboxylate, 3.65 g (0.0240 mole) of DBU and 150 ml of THF is held at reflux for 18 hours and concentrated. The residue is dissolved in ether and washed with diluted hydrochloric acid, dried (MgSO4) and concentrated. The residue is kugelrohr distilled at 0.1 torr to give 4.80 g (50%) of the desired product.

DESCRIPTION OF THE INVENTION

As in the Comparative Example above, the process of this invention is illustrated in detail below with reference to the preparation of the specific pyridine dicarboxylate compound prepared in Example 16 of U.S. Pat. No. 4,692,184.

To improve yield of the desired pyridine dicarboxylate product, the following process of the present invention generally employs the same reaction steps as Scheme I. According to the present invention, the final step of the process of Scheme I, dehydrofluorination of the dihydropyridines prepared in the previous step to afford the final pyridine dicarboxylate product, is accomplished by treatment with DABCO in contrast to the prior art dehydrofluorination step which employs DBU or 2,6-lutidine as the organic base.

In this process step, DABCO may be employed in either stoichiometric or catalytic amounts. Because DABCO is a difunctional base, the stoichiometric DABCO method uses at least one half mol of DABCO per mol of starting IVA. Use of about one mol of DABCO is preferred. The catalytic DABCO method, on the other hand, employs substantially less DABCO such as about 0.01 to less than 0.50, and preferably about 0.05 to about 0.20 mol DABCO per theoretical mol of dihydropyridines (i.e., per mol of original IVA) in conjunction with an amount of an additional base which is adequate to effect substantially complete dehydrofluorination. The additional base used in the process in which DABCO is employed as a catalyst is a base selected from the group consisting of KOH, NaOH, $K_2CO_3$, $Na_2CO_3$, $Ca(OH)_2$, triethylamine, and tributylamine. Use of a catalytic amount of DABCO thus may result in a substantial economic benefit in the process.

Whichever dehydrofluorination method is employed, it is desirable to have some water present in the process to act as a solvent for salts (such as, for example, the hydrofluoride salt of DABCO and/or of the additional base if one is used) which may be formed in the process.

Whichever specific dehydrofluorination method is used, it is desirable to conduct this process step in the presence of an inert aprotic solvent Such solvents include, but are not limited to, benzene, toluene, xylenes, cyclohexane, monochlorobenzene, butyronitrile, and like solvents. Moreover, while the temperature used in this process step is not particularly critical, it is preferred to use temperatures in the range of 50° C. to 120° C., preferably 60° C. to 90° C.

Using the stoichiometric DABCO dehydrofluorination method, the toluene solution from Step 2 is sparged vigorously with nitrogen to minimize oxidation by-products. DABCO in an aqueous solution preferably at or near saturation in a ratio greater than 0.50 mol, and preferably about 1 mol per estimated mol of dihydropyridine is likewise sparqed with nitrogen, and the two solutions are combined.

EXAMPLE 1

To a 3 L flask was added 502 g (1.2 mol) of diethyl 1,4-dihydro-2,6-bis(trifluoromethyl)-4-(2-methylpropyl)-3,5-pyridinedicarboxylate in 600 g of toluene. This solution was sparged subsurface with $N_2$ for 30 minutes. Subsequently, 146 g (1.3 mol) of DABCO and 219 g of $H_2O$ were added as an aqueous solution. The reaction mixture was heated at 75°–80° C. for 4.75 hours while it was monitored for completion by GC. At completion of the reaction, the mixture was cooled to 50° C. and the aqueous phase was removed. The toluene solution was washed with 130 g of a 15% brine solution, and the pH of the aqueous phase was adjusted to 4–5 with a small amount of concentrated sulfuric acid. The aqueous phase was then removed to leave a toluene solution of the desired product. Assay of the reaction mixture indicated the presence of 454 g (95%) of diethyl 2-difluoromethyl-4-(2-methylpropyl)-6-trifluoromethyl-3,5-pyridinedicarboxylate.

The experimental procedure above is representative of the procedure for the use of DABCO in the dehydrofluorination reaction. Additional examples utilizing different amounts of the base, solvents, and temperatures are included below. All materials were charged on the basis of the amount of dihydropyridine starting material used.

| Example | Mols DABCO | Solvent | Temp (°C.) | Time (h) | Yield (%) |
|---|---|---|---|---|---|
| 2 | 1.1 | toluene | 90 | 2 | 100 |
| 3 | 1.1 | toluene | 70 | 6 | 95 |
| 4 | 1.1 | toluene | 50 | 7 | 93 |
| 5 | 1.5 | methylcyclohexane | 70 | 3 | 83 |
| 6 | 1.5 | $CCl_4$ | 70 | 3 | 73 |
| 7 | 1.25 | toluene/water | 70 | 2 | 86 |
| 8 | 1.0 | toluene/water | 90 | 3 | 86 |
| 9 | 0.6 | toluene/water | 80 | 3 | 85 |

While the process of this invention has been specifically illustrated in terms of a specific pyridine dicarboxylate product, it is equally applicable to the preparation of other pyridine compounds. Selection of the aldehyde starting material will, of course, determine the substituent at the 4-position of the final pyridine product. Likewise it is evident that lower alkyl trifluoroacetoacetate esters other than the ethyl ester may equally well be employed. Accordingly, the scope of this invention is to be limited only in accordance with the annexed claims.

We claim:

1. A process for preparing a 4-(lower alkyl)-2-difluoromethyl-6-trifluoromethyl-3,5-pyridinedicarboxylic acid ester from a dihydropyridine starting material having the above substituents at the 3-, 4-, 5-, and 6-positions and having a trifluoromethyl substituent at the 2-position, which comprises contacting the starting material dissolved in an inert aprotic solvent with at least one half its molar amount of 1,4-diazabicyclo-[2.2.2]-octane (DABCO) in the presence of water in an amount sufficient to dissolve the resulting fluoride salt of said octane compound.

2. A process according to claim 1 wherein the amount of DABCO is about 1.0 times the molar amount of the dihydropyridine starting material.

3. A process according to claim 2 wherein the DABCO is in the form of an aqueous solution.

4. A process according to claim 3 wherein the process is conducted in an inert aprotic solvent.

5. A process according to claim 4 wherein the aprotic solvent is selected from benzene, toluene, xylenes, methylcyclohexane, monochlorobenzene, and butyronitrile.

6. A process according to claim 3 or 4 wherein the process is conducted in the substantial absence of molecular oxygen.

7. A process for preparing 2-difluoromethyl-6-trifluoromethyl-4-(2-methylpropyl)-3,5-pyridinedicarboxylic acid esters selected from dimethyl and diethyl esters from a dihydropyridine starting material having the above substituents at the 3-, 4-, 5-, and 6- positions and having a trifluoromethyl substituent at the 2-position, which comprises contacting the starting material dissolved in an aprotic solvent with at least one half its molar amount of 1,4-diazabicyclo-[2.2.2]-octane (DABCO) in the presence of water in an amount sufficient to dissolve the resulting fluoride salt of said octane compound.

8. A process according to claim 7 wherein the amount of DABCO is about 1.0 times the molar amount of the dihydropyridine starting material.

9. A process according to claim 8 wherein the DABCO is in the form of an aqueous solution.

10. A process according to claim 9 wherein the process is conducted in an inert aprotic solvent.

11. A process according to claim 10 wherein the aprotic solvent is selected from benzene, toluene, xylenes, methylcyclohexane, monochlorobenzene, and butyronitrile.

12. A process according to claim 9 or 10 wherein the process is conducted in the substantial absence of molecular oxygen.

* * * * *